United States Patent [19]

Christensen

[11] Plant 4,663

[45] Mar. 10, 1981

[54] ROSE PLANT

[75] Inventor: Jack E. Christensen, Ontario, Calif.

[73] Assignee: Armstrong Nurseries, Inc., Ontario, Calif.

[21] Appl. No.: 89,201

[22] Filed: Oct. 29, 1979

[51] Int. Cl.[3] ..... A01H 5/00
[52] U.S. Cl. ..... Plt./7
[58] Field of Search ..... Plt./7

*Primary Examiner*—Robert E. Bagwill

*Attorney, Agent, or Firm*—William H. Elliott, Jr.; Andrew R. Klein

[57] ABSTRACT

A rose plant of the hybrid miniature class, having a vigorous tall upright habit of growth, for roses of this class, and producing flowers, sometimes singly but usually up to four or more blooms per stem, the blooms being deep orange in color. There are from 15 to 20 petals, of round to obovate shape. The plant is a hardy dwarf bush seedling, of the outdoor type. The open flower has a slight tea fragrance.

1 Drawing Figure

This invention relates to a new class of hybrid miniature rose. The plant is a hardy outdoor seedling of the dwarf bushy type, cultivated for garden decoration. It was propagated by Jack E. Christensen in Ontario, Calif., having as its seed parent "Anytime" and, as its pollen parent, "Katherine Loker". It holds its distinguishing characteristics through succeeding propagations by cuttings and by buddings.

The new variety bears its flowers sometimes singly, but usually four or more blooms to a stem, in irregular clusters on strong medium to long stems. The plant blooms abundantly outdoors and nearly continuously during the growing season. It has a slight tea fragrance in open flower.

This new miniature rose cultivar may be distinguished from its seed parent, Anytime, by the following combination of characteristics:

Anytime bears flowers of relatively uniform coral orange coloration, whereas the new rose bears flowers of deep orange coloration essentially as described herein.

Anytime has a narrowly obovate petal shape, whereas the new rose has a round to broadly obovate petal shape.

Though both cultivars are miniatures, the new cultivar has a tall, upright plant habit, whereas Anytime has a low spreading habit.

This new miniature rose cultivar may be distinguished from its pollen parent, Katherine Loker, by the following combination of characteristics:

Katherine Loker bears flowers of relatively uniform yellow coloration, whereas the new rose bears flowers of deep orange coloration.

The new cultivar is classed as a hybrid miniature rose, whereas Katherine Loker is in the hybrid floribunda class.

Katherine Loker bears significantly larger flowers of 3½ to 4½ inch diameter, whereas the new cultivar bears flowers of 1 to 1½ inch diameter.

Katherine Loker has significantly more petals, from 20 to 26, than does the new rose, which has from 15 to 20.

The accompanying drawing illustrates the plant in color and shows the flowering thereof from bud to full bloom.

Throughout this specification, color names beginning with a small letter signify that the name of that color, as used in common speech, is aptly descriptive. Color names beginning with a capital letter designate values based upon the Nickerson Color Fan, put out by Munsell Color Co.

BUD

The peduncle is of average length for miniature roses and from average to heavy caliper, being erect and stiff and almost smooth, with some stipitate glands. The color ranges from Moderate Brown, 5YR3/3, to Moderate Yellow Green, 5GY5/6.

Before the calyx breaks, the bud is medium in size for miniature roses, of medium length, pointed and ovoid, with some foliaceous appendages and stipitate glands on the surface of the bud. There are usually slender foliaceous parts extending beyond the tip of the bud equal to one-fourth of its length.

As the calyx breaks, the color is near Strong Reddish Orange, 7.5R6/12. The inner surface of the sepals carries a fine tomentum; margins of sepals are lined with stipitate glands and hairs.

As the first petal opens, the bud is of average size for miniature roses, medium-length, flat to urn-shaped. The base of both the inside and outside petals is of near Brilliant Yellow, 5Y9/9, suffusing to between Strong Reddish Orange, 10R5/11, and Strong Reddish Orange, 7.5R5/13, on the outside petal, while the majority of the inside petal is a color between Strong Reddish Orange, 10R6/12, and Strong Reddish Orange, 10R5/11. The bud opens up well and is not prevented from opening by cold, hot, wet or dry weather.

BLOOM

The size of the bloom when fully open is from average to large for miniature roses, being from 1 to 1.5 inches. The petalage is double, with from 15 to 20 petals, plus from 0 to 5 petaloids arranged regularly. The bloom is flat and cupped at first, becoming open to cupped, the petals remaining at first tightly cupped and becoming later at maturity loosely cupped.

The petals are thick, with inside slightly satiny and outside slightly shiny to satiny. The outside petals are round to broadly obovate, with slightly mucronate apex. The intermediate petals are broadly obovate, with slightly mucronate apex. Inside petals are obovate to irregular. The colors may be modified by being blotched, shaded and/or washed or tinted, with other colors.

The paragraphs immediately following describe color values observed in a flower newly opened in the month of July. The plant had been grown outdoors in Ontario, Calif.

The color of the outer surface of the outside petal was near Brilliant Yellow, 5Y9/9, at the base, suffusing to between Strong Reddish Orange, 10R6/12, and Strong Reddish Orange, 7.5R6/12. The outer surfaces of the intermediate and inside petals were colored the same way.

The color of the inner surface of the outside petal was near Vivid Yellow, 5Y8/12, at the base, with most of the petal between Strong Reddish Orange, 10R5/11, and Strong Reddish Orange, 10R6/12. The inner surfaces of the intermediate and inside petals were colored the same way.

The paragraph immediately following describes the color values observed in a bloom which had been open for three days, outdoors, in the month of July. The plant had been grown outdoors in Ontario, Calif.

The outer surface of the outside petal was near Brilliant Greenish Yellow, 7.5Y9/8, at the base, suffusing to near Strong Reddish Orange, 7.5R6/12. The outer surface of the inside petal was colored the same way. The inner surface of the outside petal was near Brilliant Greenish Yellow, 7.5Y9/8, at the base, the remainder of the petal being near Strong Reddish Orange, 7.5R5/13. The inner surface of the inside petal was colored the same way.

The general color effect of the newly opened flower is near Strong Reddish Orange, 10R5/11. The bloom after being three days open gives a general color effect which is near Strong Reddish Orange, 7.5R5/13. The petals persist, fading to near Strong Reddish Orange, 7.5R6/12. They are not particularly affected by cold, hot, wet, or dry weather.

The flower on the bush in the garden persists for from 4 to 5 days in the month of June, in the locality named. Cut roses grown outdoors and kept indoors last from 3 to 4 days in June.

REPRODUCTIVE ORGANS

The stamens are from average to many in number and are arranged regularly about the pistils, a few being tucked in the calyx.

The filaments are medium length and near Vivid Yellow, 2.5Y8/12, in color. Most are with anthers.

The anthers are medium size, all opening approximately at once. Their outer edge is near Vivid Yellow, 2.5Y8/12, in color, while the interior surface is near Brilliant Greenish Yellow, 7.5Y9/8.

The pollen is abundant, and near Vivid Yellow, 2.5Y8/12, in color.

The pistils are average in number, there being approximately 50.

The styles are uneven, of average length to long, thin to average caliper and loosely bunched. They are near Brilliant Yellow Green, 2.5GY9/8, in color.

The coloration of the stigma is near Strong Greenish Yellow, 10Y8/11.

Usually, most of the ovaries are enclosed in the calyx, while some protrude therefrom.

Immature hips were of average length, globular and near Strong Yellow Green, 5GY6/8, in color. They were very smooth, with thick fleshy walls.

Hip sepals are permanent, medium-length to long and spear-shaped. On the inside they are near Strong Yellow Green, 2.5GY6/8, in color, with a central area of near Dark Red, 2.5R3/7, and a gray bloom. On the outside the color is between Strong Yellow Green, 5GY6/8, and Moderate Yellow Green, 5GY5/6.

There are from an average number to many seeds, for miniature roses, being from 4 to 10 in number, and of medium size.

FOLIAGE

The compound leaves usually comprise 3 to 5 leaflets. They are from normal to abundant, medium size to large, and from heavy to somewhat leathery and glossy. The leaflets are oval, with apex acuminate, base acute, and margin doubly serrate.

The mature foliage displays upon its upper surface a coloration which is between Grayish Olive Green, 7.5GY3/2, and Dark Green, 5G3/4. The under surface is near Moderate Olive Green, 7.5GY4/4, washed with gray.

The young foliage on its upper surface is near Moderate Olive Green, 7.5GY4/4, suffused heavily with near Dark Red, 2.5R3/7. On its under surface the color is near Dark Red, 2.5R3/7, with some gray.

The rachis is average in size, the upper side being grooved, with a few stipitate glands on the edges. The under side is moderately smooth, with stipitate glands.

The stipules are long, medium-width, and with medium-length to long points turning out at an angle of more than 45°.

The plant displays a more than average resistance to mildew, when compared with other varieties now in commerce under comparable conditions, when grown at Ontario, Calif.

GROWTH

The plant is a bushy dwarf, upright in habit and much branched. It displays a very vigorous growth. The canes are of medium to heavy caliper, for miniature roses.

The main stems are between Moderate Yellow Green, 2.5GY5/5, and Moderate Olive Green, 2.5GY4/3, in color. They bear few large prickles, which are short to medium-length, almost straight to hooked slightly downward, with moderately long and narrow base. The color is between gray and Brownish Gray, 10YR3/1. There are several small prickles which are the same coloration as the large prickles. There are no hairs.

The branches are a color between Strong Yellowish Green, 10GY5/8, and Moderate Yellow Green, 5GY5/6. They bear a few large prickles which are short to medium-length, almost straight to hooked slightly downward, with moderately long and narrow base. The color is between Brownish Orange, 5YR5/8, and Strong Brown, 5YR4/5. There are several small prickles which are the same coloration as the large prickles. There are no hairs.

New shoots have a coloration near Moderate Olive Green, 2.5GY4/3, washed lightly with near Dark Red, 2.5R3/7. There are a few large prickles which are medium-length, almost straight to hooked slightly downward, with moderately long and narrow base. The color is near Moderate Red, 2.5R4/10. There are several small prickles which are the same coloration as the large prickles. There are a few hairs, which are also the same coloration as the large prickles.

I claim:

1. A new and distinct variety of miniature rose plant, substantially as herein shown and described, and being particularly characterized in that the plant has a vigorous, tall and very upright habit of growth, with strong stems which may bear up to four or more flowers, the overall color effect, both in bud and in flower, being deep orange, the blooms being large for roses of this class, ranging from 1.0 to 1.5 inches in diameter, and comprising from 15 to 20 round to broadly obovate petals.

* * * * *

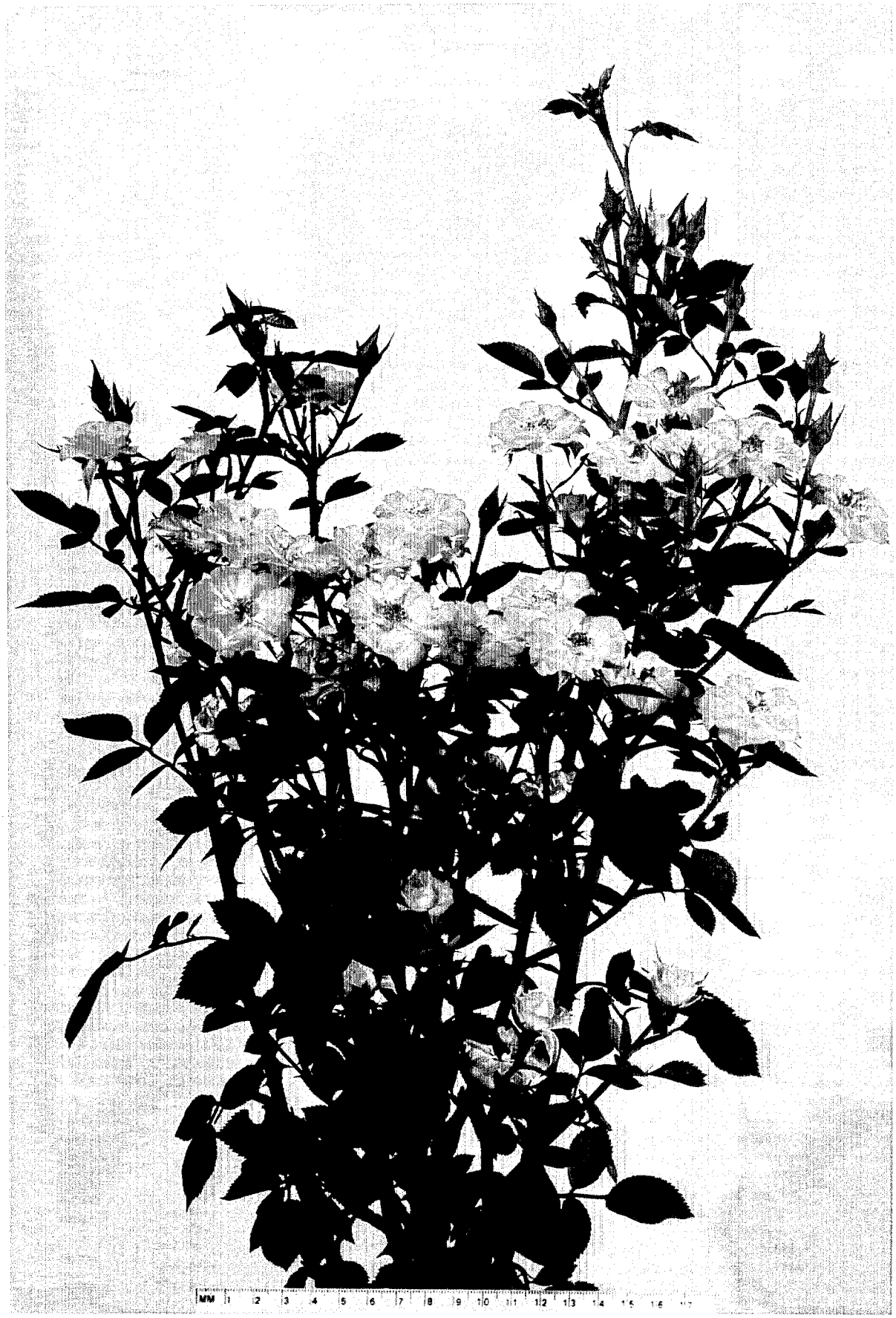
MM 1 2 3 4 5 6 7 8 9 10 11 12 13 14 15 16 17